United States Patent [19]
Shih

[11] Patent Number: 5,660,544
[45] Date of Patent: Aug. 26, 1997

[54] METHOD AND APPARATUS OF RECORDING AND REPRODUCING THE PATH OF INSERTION OF A CAST ON SURVEYORS

[76] Inventor: Jui-Yuan Shih, No. 179, Min Tsu Rd., Lu Kang Chen, Changhua Hsien, Taiwan

[21] Appl. No.: 372,324

[22] Filed: Jan. 13, 1995

[51] Int. Cl.⁶ .................................................. A61C 11/00
[52] U.S. Cl. .................................. 433/55; 433/57; 433/62
[58] Field of Search .................................. 433/54, 55, 56, 433/58, 60, 62, 64, 65, 72, 66

[56] References Cited

U.S. PATENT DOCUMENTS

| | | | |
|---|---|---|---|
| 3,409,986 | 11/1968 | Freeman | 433/55 |
| 4,189,835 | 2/1980 | Seldin | 433/55 X |
| 4,812,118 | 3/1989 | Creekmore | 433/55 X |
| 5,257,932 | 11/1993 | Leinfelder et al. | 433/55 X |

OTHER PUBLICATIONS

Wagner, et al., A Study of Four methods of Recording the Path of Insertion of Removable Partial Dentures, J. Prosthet. Dent., vol. 35, No. 3, pp. 267–272, Mar., 1976.

Kaloyannides, Reproduction of Tilt of a Cast on a Surveyor, J. Prosthet. Dent., vol. 30, No. 4, pp. 465–467, Oct., 1973.

Steas, Recording and Reproducing the tilt of a Cast on a Surveyor, J. Prosthet. Dent., vol. 57, No. 1, pp. 121–125, Jan., 1987.

McGivney GP, Castleberry, McCracken's Removable Partial Prosthodontics, 8th ed., pp. 194–198, The C.V. Mosby Company, 1989.

*Primary Examiner*—Nicholas D. Lucchesi
*Attorney, Agent, or Firm*—Beveridge, DeGrandi, Weilacher & Young, LLP

[57] ABSTRACT

The present disclosure relates to a method and an apparatus for recording and reproducing the path of insertion of a cast on surveyors. In the method, the accuracy and speed of recording the path of insertion is easily effected with the help of a scoring tool and an adjustable surveyor table on which a cast is secured and the spatial relationship of the cast with respect to the scoring tool can be easily adjusted, facilitating parallel line making on the cast in one aspect and the reorientation of the cast in another aspect.

20 Claims, 21 Drawing Sheets

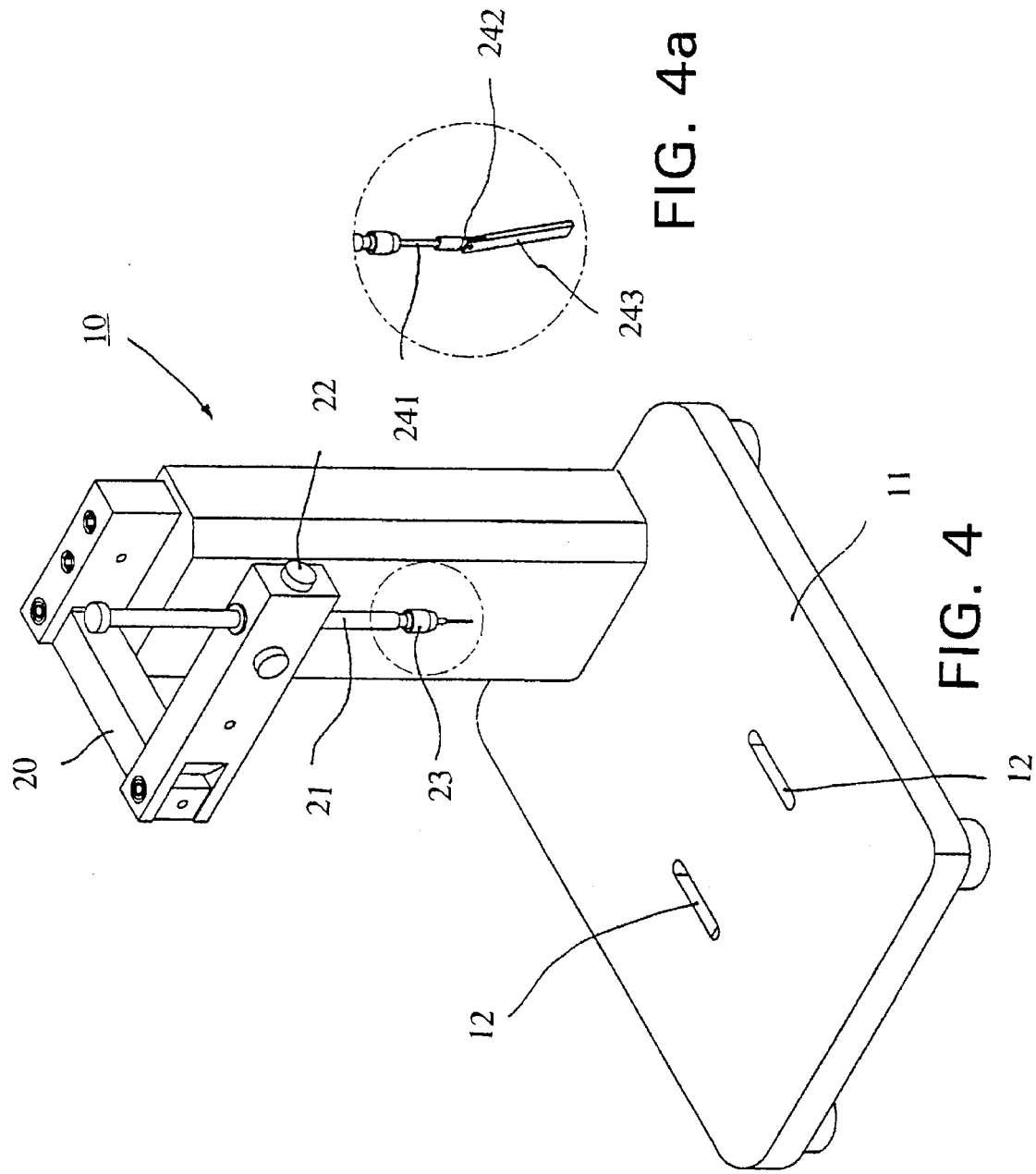

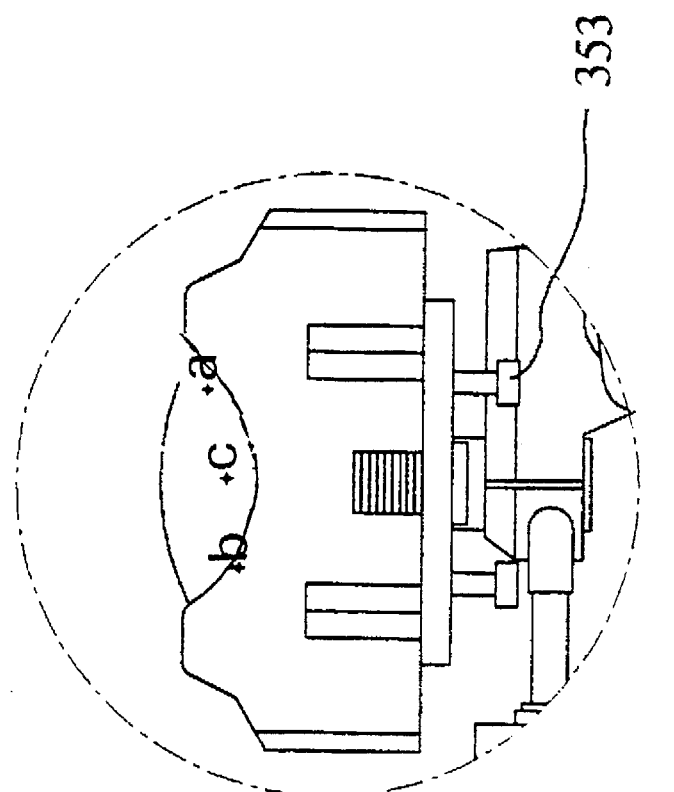
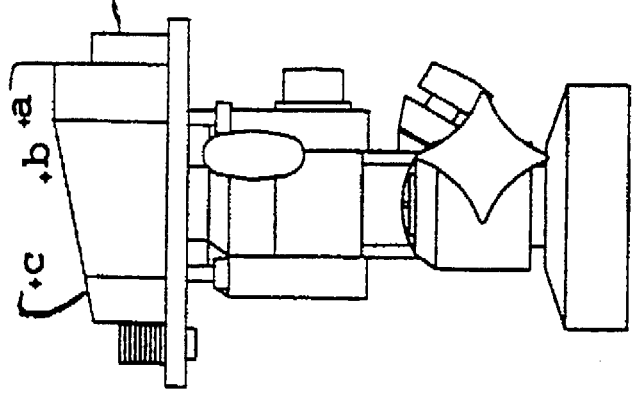
FIG. 19a
FIG. 19

METHOD AND APPARATUS OF RECORDING AND REPRODUCING THE PATH OF INSERTION OF A CAST ON SURVEYORS

BACKGROUND OF THE INVENTION

The present invention relates to a method and an apparatus of recording and reproducing the path of insertion of a cast on dental surveyor.

As it has been well known that there have been several methods disclosed in this dental field for recording the path of insertion of a cast and the reproduction of the tilt on surveyor, such as:

1. Tripod-marks method
2. Vertical lines on sides of base of cast method (scoring method)
3. Three marks on sides of base of cast method
4. Cemented pin method (Ref: 1)
5. Kaloyannides method (Ref: 2)
6. Steas method (Ref: 3)

Among these methods, the vertical lines on sides of a base of cast method (scoring method) has a preferred advantage, i.e., its records can be easily reproduced in any duplication. However, it is not easy to accurately reproduce the tilt of cast on a surveyor, because there are two problems existing in this method. First, the records made on sides of base are done by scoring along a analyzing rod, it may shift to either sides, if there is a space left between the analyzing rod and the cast surface, as shown in FIGS. 1a–1c second, redetermination of the position of the cast on surveyor can be done only by trial and error approach; such procedure is time consuming and the result is not very satisfactory. In the tripod-marks method, it encounters the same problems too.

To make records in the vertical lines on sides of a base cast method (scoring method) accurate, they must be scored perpendicular to the cast surface. In other words, it should be a projection of the analyzing rod on the cast surface. Without other aids, it is difficult to get this job done simply by scoring the cast surface along the edge of the analyzing rod, because there may be a space left between the analyzing rod and the cast surface.

Solution to this problem is, above all, to make the cast surface on which marks are scored trimmed into a flat plane, since it is impossible to scribe a straight line on a curved surface. To aid in making a vertical line, a square block can be used. Making a vertical line, the base of the square block should be in close abutment with the cast surface, one side of it is positioned alonside of the analyzing rod, then the vertical line can be made by scribing along the other side of the block. The records made in this manner will be the projection of the analyzing rod off the cast surface, as shown in FIGS. 2a–2c.

In order to simplify this procedure, a special scoring tool is designed with the same geometric concept.

In general, there are two most common methods for reproducing the original cast position on surveyors given as below:

The scoring method:

Tilting a cast until all three lines marked thereon become again parallel to the analyzing rod, the original cast position can be reestablished. In other words, first, the cast is oriented in adjustment until one line on the base of the cast becomes parallel to the analyzing rod, then it is tried to make the lines on the lateral surfaces of the cast parallel to the analyzing rod. When the east position is altered, all the lines on the cast surfaces will be moved in unison, it is almost impossible to maintain the parallel relationship of the line on the base of the cast with the analyzing rod, having already been established, it will be shifted to either side. By means of a conventional surveyor table equipped with a universal joint, as shown in FIG. 3, an operator can reproduce the tilt of a cast only by trial and error, until all three lines are again parallel to the analyzing rod.

The tripod-mark method:

On returning the cast to the surveyor, it may be tilted until the tip of the analyzing rod again contacts the three dots on the same plane. However, the procedure is not very easy because to make three dots locate on an identical level at one time without trial and error. So, it is necessary to find an easy way to quickly and accurately determine a cast position by way of a new surveyor table.

SUMMARY OF THE INVENTION

The primary object of the present invention is to provide an easy and efficient method of recording and reproducing the path of insertion of a cast on dental surveyors.

Another object of the present invention is to provide an adjustable surveyor table in combination with a conventional surveyor so as to permit a cast to be easily secured to a cast mounting platform and the spatial relation of the cast with respect to a scoring tool can be variably adjusted whereby the recording and reproducing the path of insertion of a cast on dental surveyors can be speedily determined.

BRIEF DESCRIPTION OF THE DRAWINGS

FIG. 3b1 is an enlarged diagram showing the scoring of a line with a conventional scoring tool in close abutment against a cast;

FIG. 3c1 is an enlarged diagram thereof;

FIGS. 4, 4a are diagrams showing a scoring tool of the present invention which can be mounted to a clamping member of a conventional surveyor;

FIGS. 8A, 8B, 8C are enlarged diagrams showing the zero setting marks on the rotation adjustment, upper joint knuckle and lower joint knuckle being set at zero degree so as to create a plane by the two parallel pillars which will be perpendicular to the long axis of the upper joint knuckle; as the upper and lower joint knuckles are set at zero degree, the cast mounting platform will be parallel to the horizontal plane;

FIGS. 19, 19a show the mounting of the cast on the cast mounting platform and setting both the upper and lower joint knuckles at zero degree;

FIGS. 20, 20a show the use of the height adjustment screws to adjust the cast position, making the two points a and b on an identical level;

DETAILED DESCRIPTION OF THE PREFERRED EMBODIMENTS

Figure 1A:
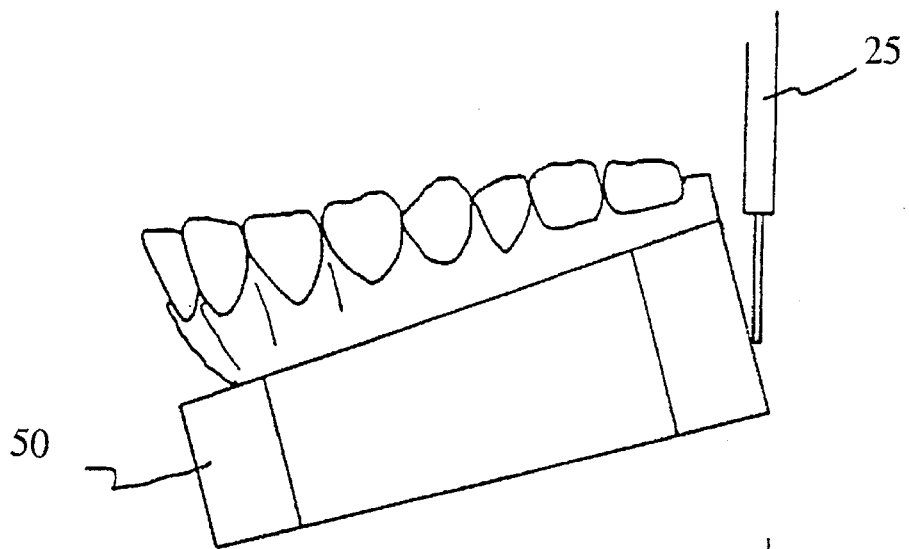
FIGS. 1a–1c are diagrams showing a prior art method of scoring lines on a cast which are scribbed along an analyzing rod with them out of parallel with one another as a result of a space left between the cast surface and the analyzing rod.
Figure 1B:
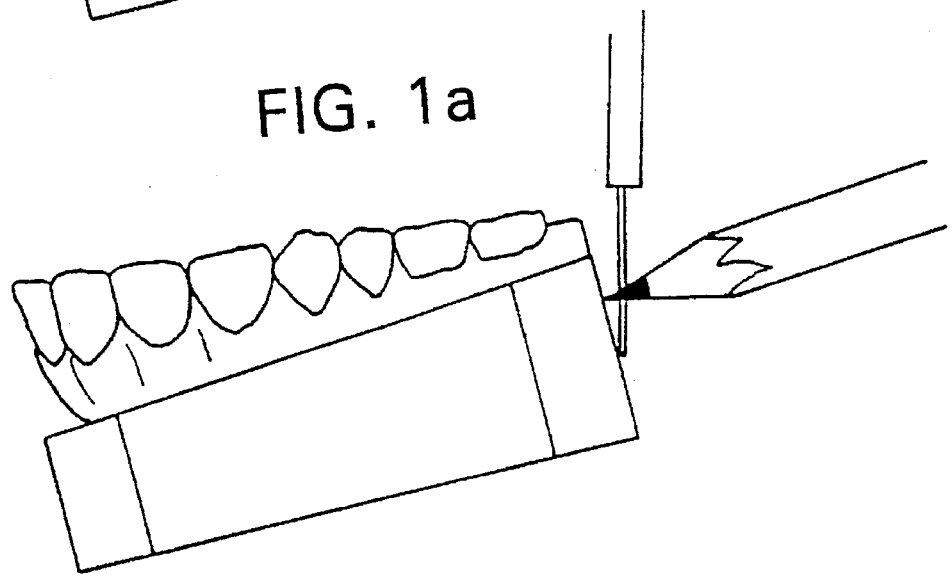
Figure 1C:
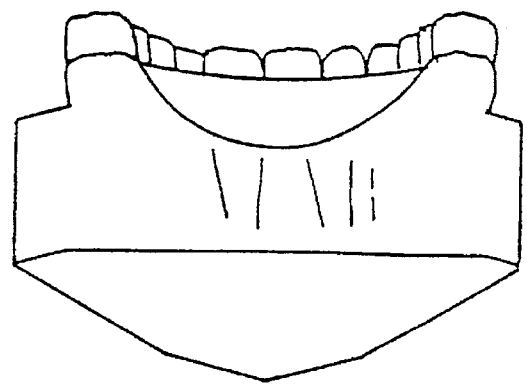
Figure 2A:
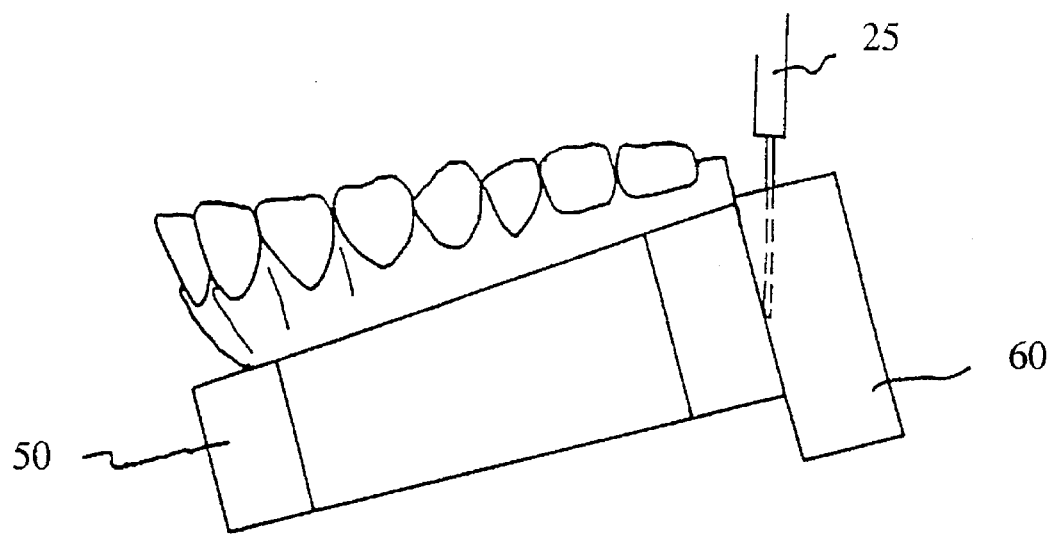
FIGS. 2a–2c are diagrams showing a square block secured to the side of an analyzing rod and is placed in close abutment against the cast surface so that lines scribbed along the other side of the block will be the projection of the analyzing rod on the cast surface with the lines parallel with one another.
Figure 2B:
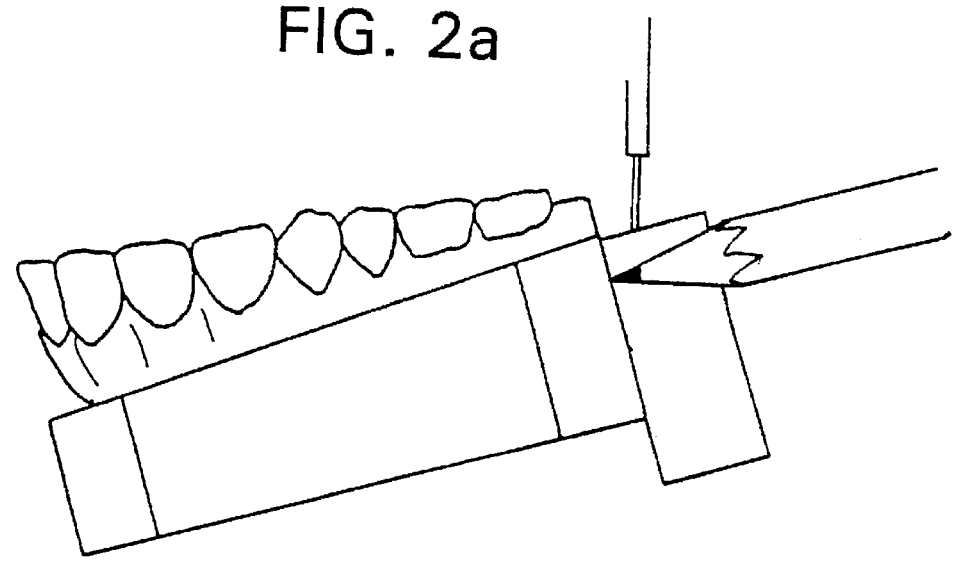
Figure 2C:
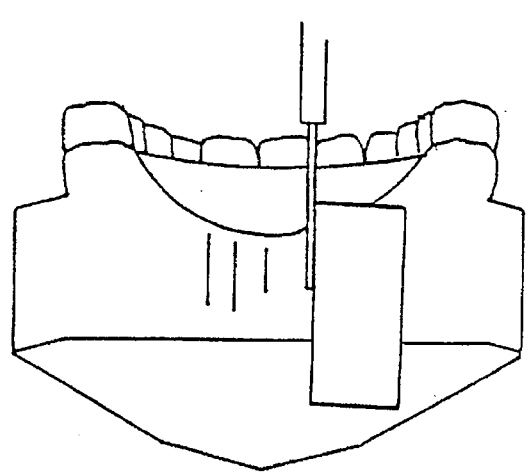
Figure 3B:
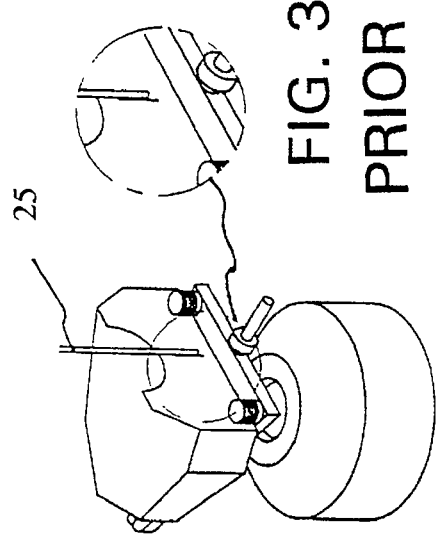
FIG. 3b is a diagram showing a cast mounted onto the surveyor table.
Figure 3C:
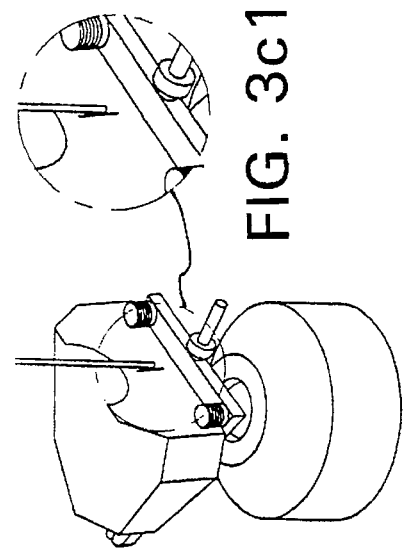
FIG. 3c is a diagram showing a dental cast mounted onto the surveyor table with the scoring tool not in close contact with a cast.
Figure 3A:
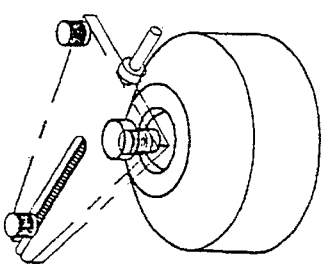
FIG. 3a is a diagram showing a prior art surveyor table.
Figure 5:
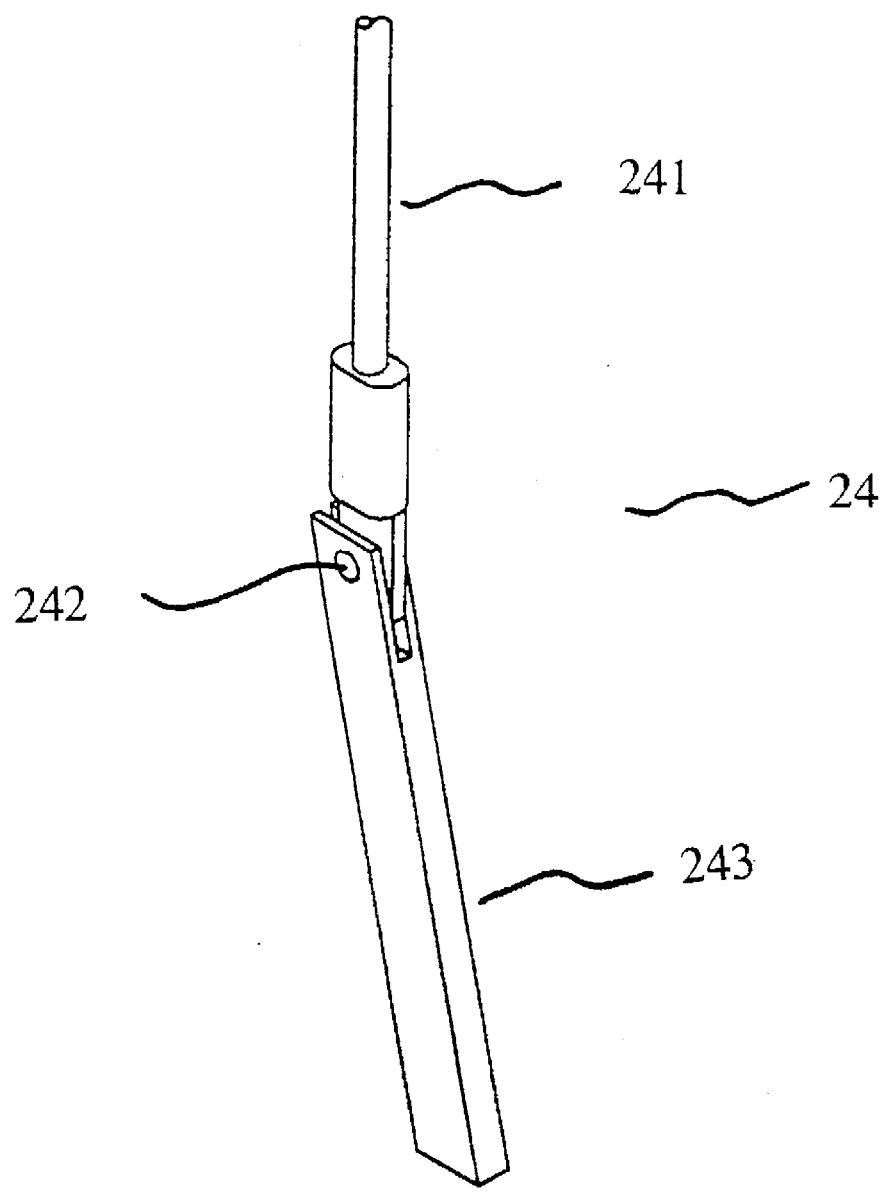
FIG. 5 is a diagram showing a scoring tool of the present invention.

Referring to FIGS. 4, 5, a special scoring tool 24 for marking precise straight lines on a cast surface is illustrated. This scoring tool 24 has two parts which are connected to each other by a hinge joint 242. The upper part has a mandrel 241 served as an attachment for a surveyor spindle, the lower part is an analyzing rod 243 having a rectangular cross sections serving the same purpose as a conventional square block as previously described.

Figure 6A:
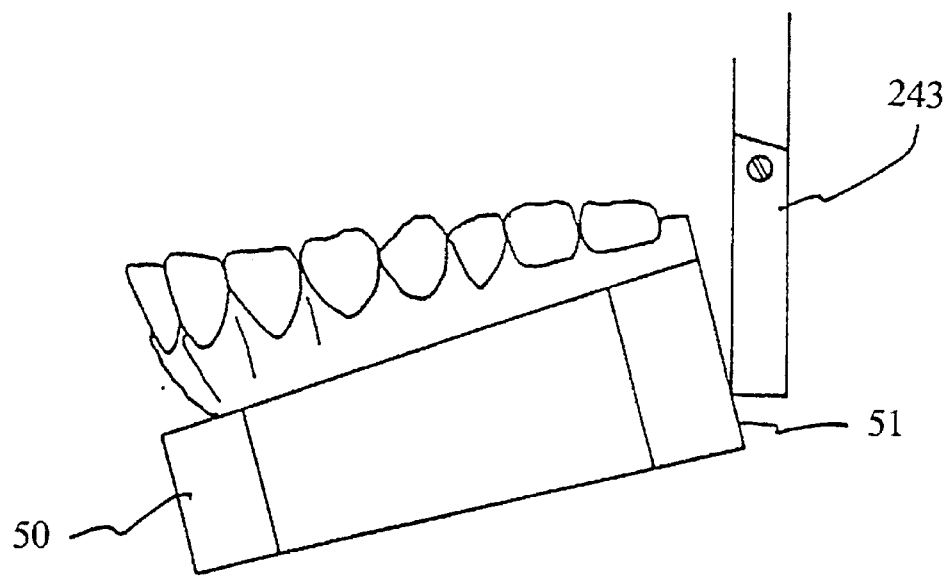
FIGS. 6a–6c are diagrams showing the steps of the lower segment of the scoring tool being adjusted to abut closely against the east surface and a line which is a projection of the analyzing rod to the cast surface is scribed along the other side thereof.
Figure 6B:
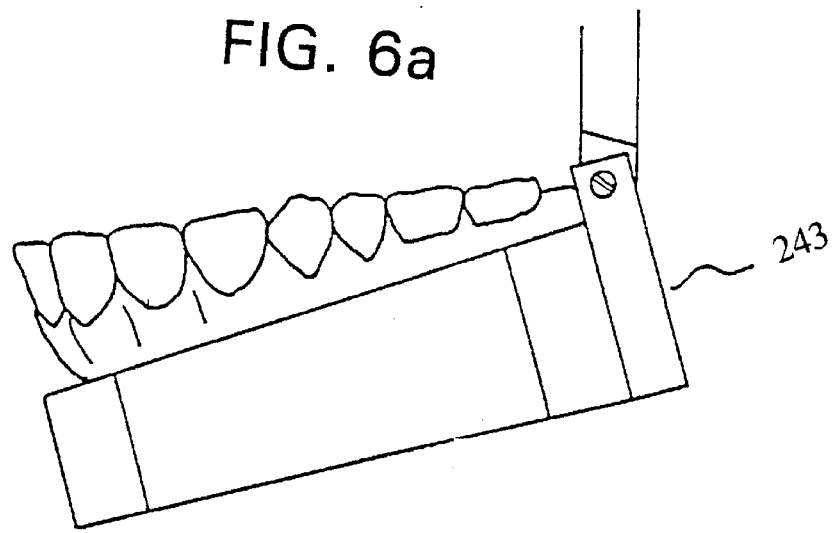
Figure 6C:
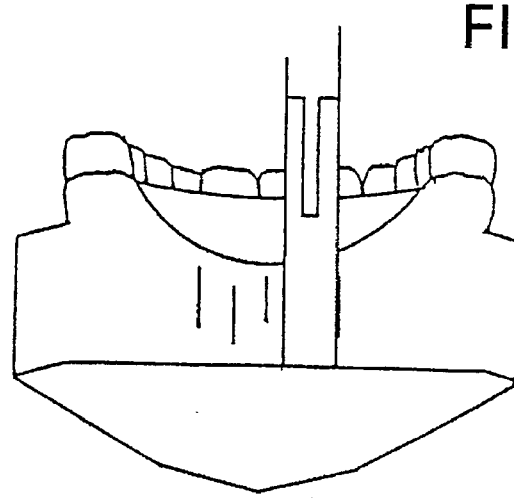

Using this scoring tool to keep record of a path of insertion, it is necessary to keep the lower part in close abutment against the cast surface of a dental model so as to permit vertical lines scribed along an edge of the lower part. Because the hinge joint is parallel to the horizontal plane, it limits the direction of movement of the lower part on the plane perpendicular to the cast surface and not to shift to either side. So, the lines marked in such manner will conform to the projection of the path of insertion on the cast surfaces, as shown in FIGS. 6a–6c.

Figure 7:
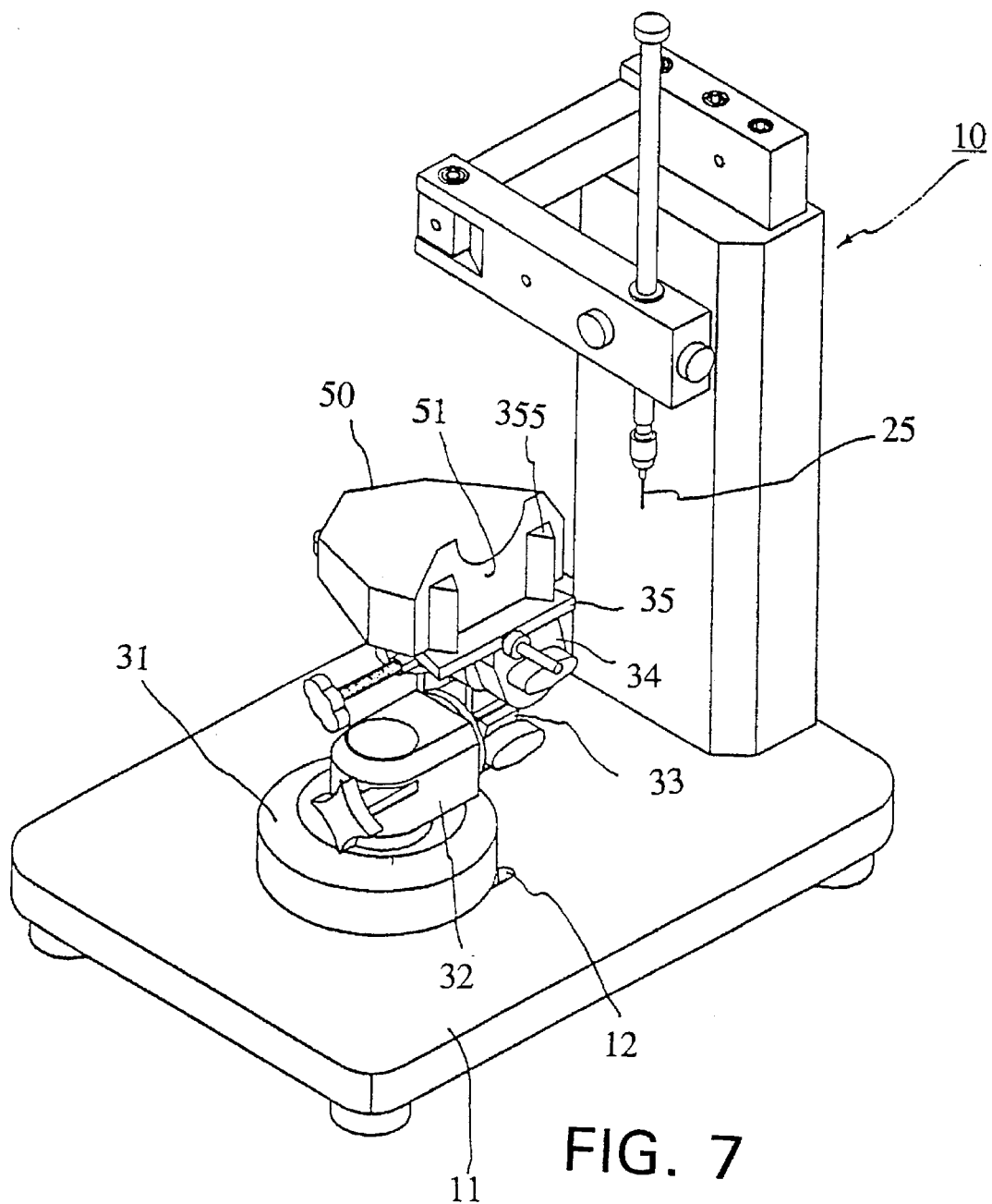
FIG. 7 is a diagram showing a surveyor table of the present invention mounted to a conventional surveyor in practical operation.
Figure 8:
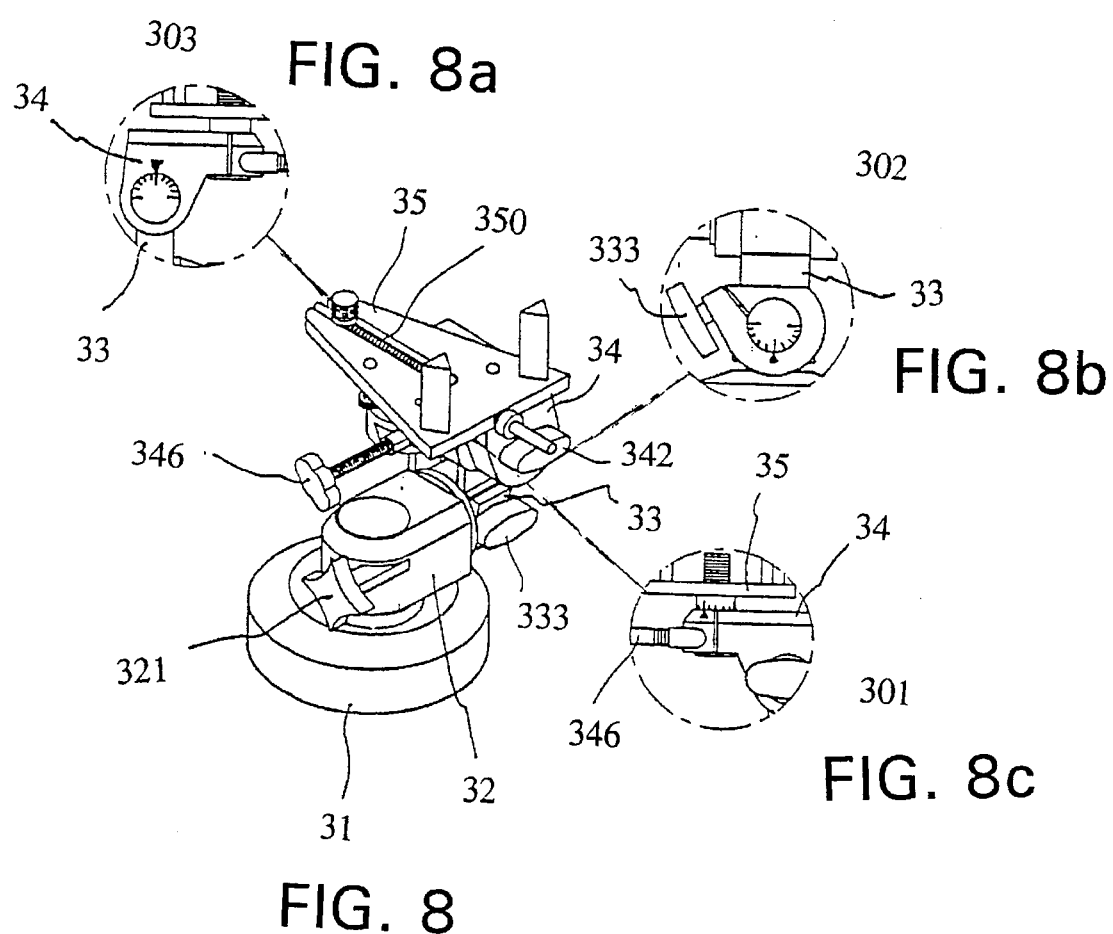
FIG. 8 is a surveyor table of the present invention.
Figure 9:
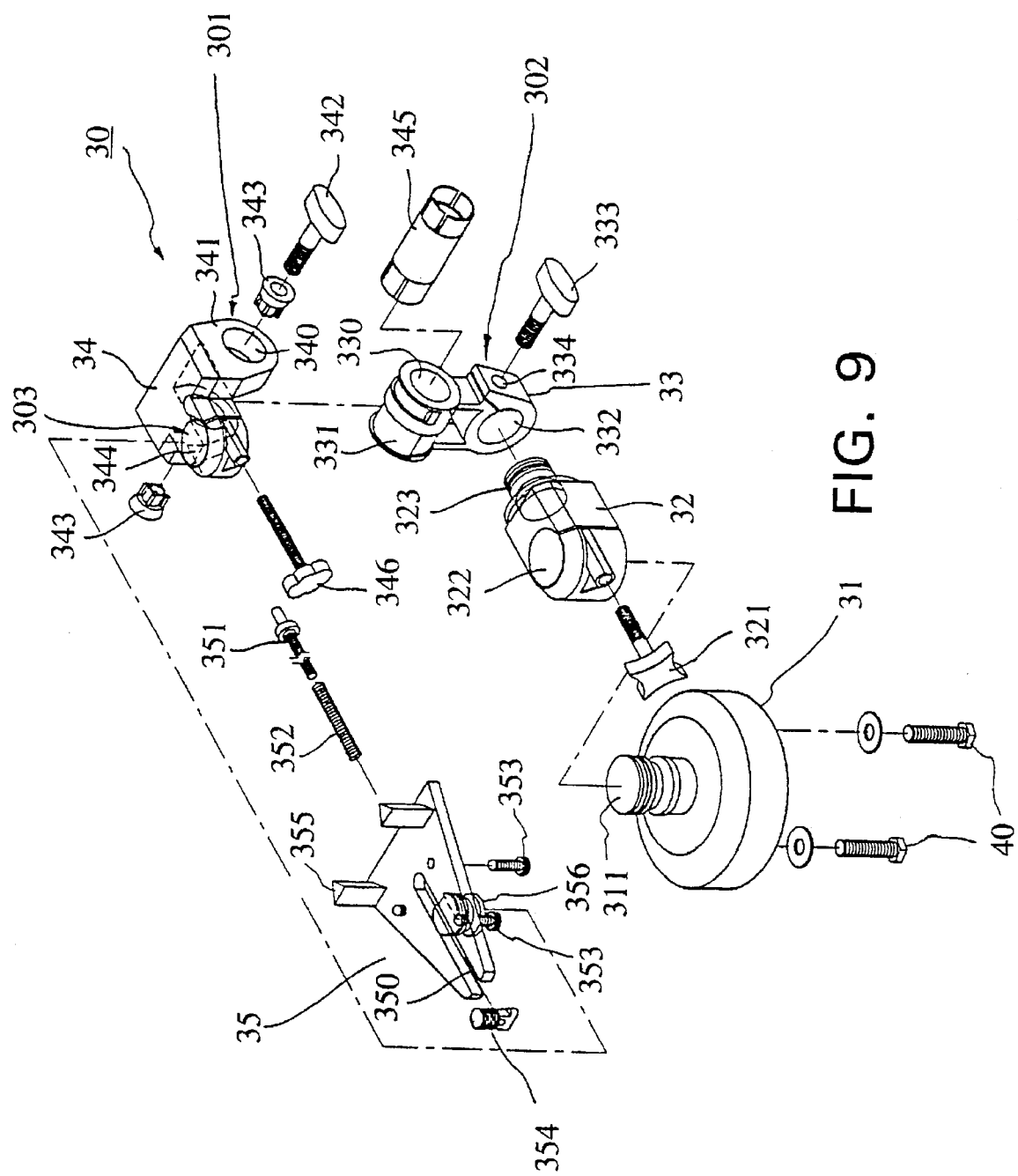
FIG. 9 is a diagram showing the exploded components of the surveyor table of the present invention.
Figures 10A, 10B:
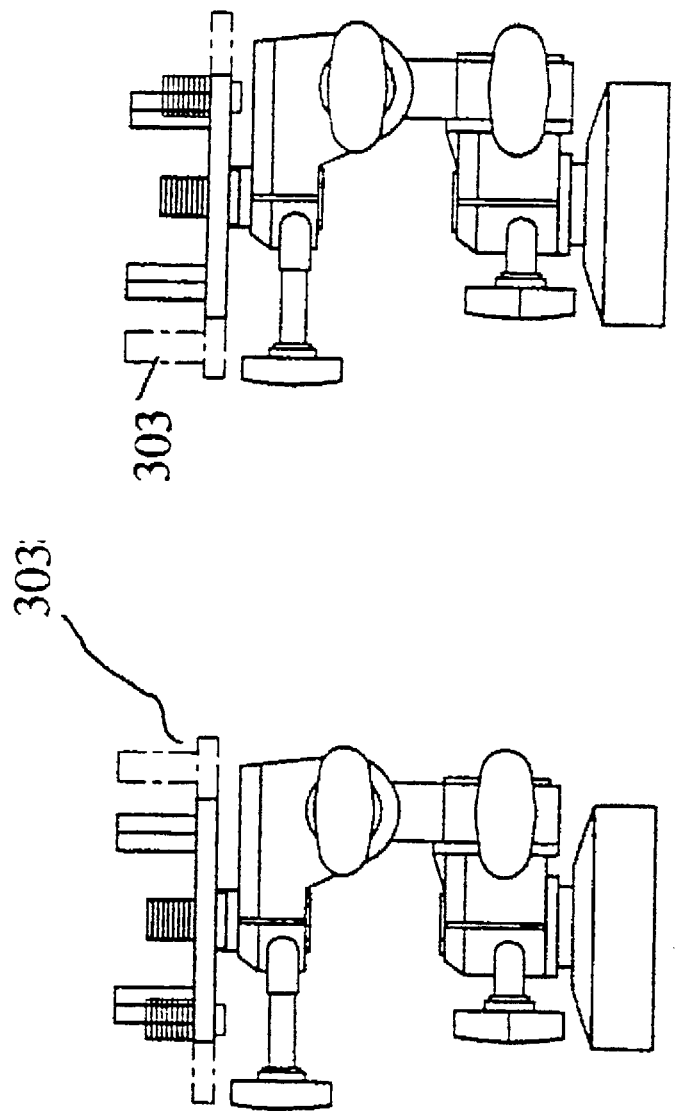
FIG. 10 is a diagram showing the cast mounting platform being rotated with respect to the upper joint knuckle controlled by the rotation adjustment.
Figures 11, 12:
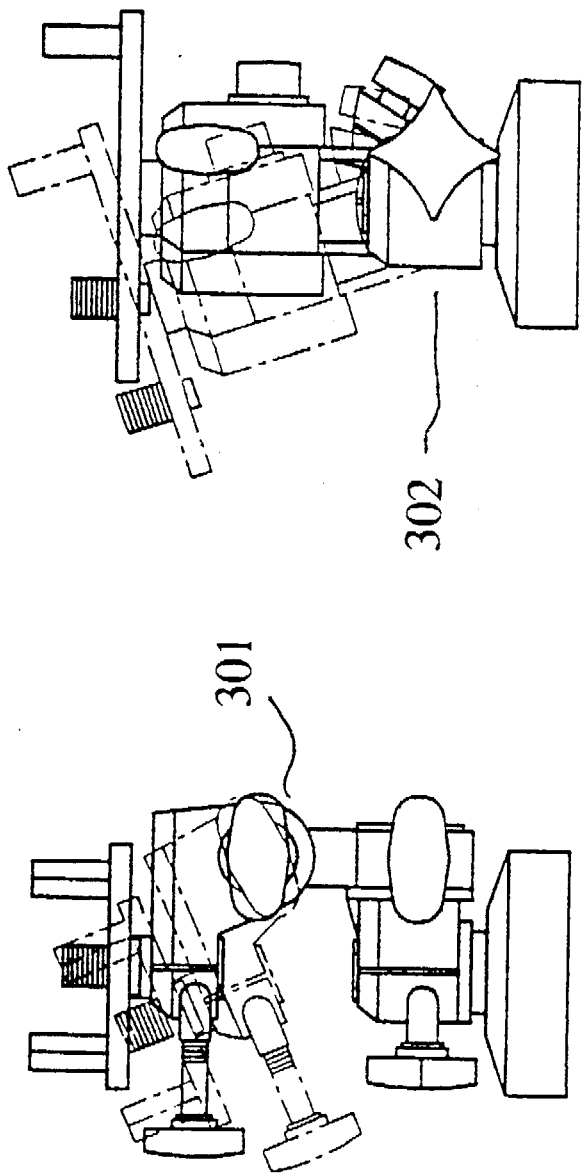
FIG. 11 is a diagram showing an adjustment of the cast mounting platform by actuation of the upper joint knuckle.
FIG. 12 is a diagram showing the cast mounting platform being adjusted by the lower joint knuckle.
Figures 13A, 13B:
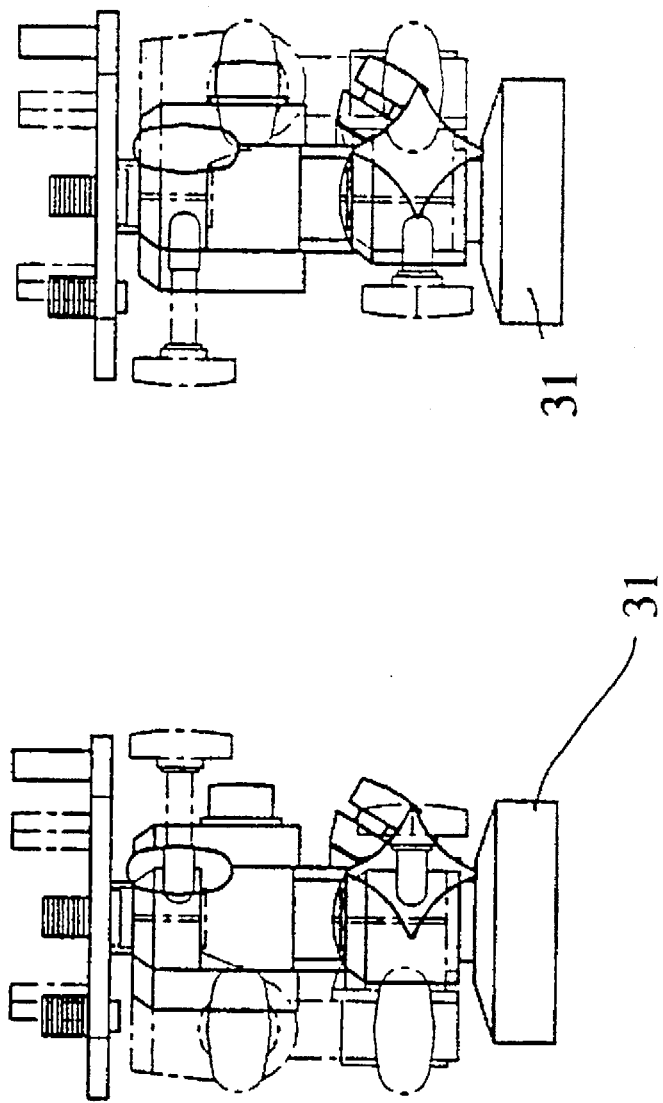
FIG. 13 is a diagram showing the adjustment of the surveyor table by way of the rotation joint knuckle with respect to the operation base.

Referring to FIGS. 7, 8, 9, a new surveyor table 30 of the present invention is provided. The surveyor 10 has a supporting base 11 on which a pair of parallel slots 12 are disposed. The surveyor table 30 is equipped with a cast mounting platform 35 on which is disposed a cast 50. A round operation base 31 is adjustably engaged with the parallel slots 12 on the supporting base 11 of the surveyor 10. On one side of the cast mounting platform 35 are disposed two parallel fixed pillars 355. At the center of the cast mounting platform 35 and in the longitudinal direction is disposed an open-ended slot 350. A cast holding clamp 354 biased by a spring 352 fixed to a bolt 351 is slidably housed in the slot 350 and three cast height adjusting screws 353.

Referring to FIGS. 10, 11, 12, 13, an upper joint knuckle 301 and a lower joint knuckle 302 and a supporting block 32 are adjustably associated with one another. The cast mounting platform 35 is rotatably engaged with the upper joint knuckle 301 by means of the rotation adjustment 303. The supporting block 32 is adjustably mounted to the operation base 31.

Referring further to FIG. 9, the upper joint knuckle 301 has bifurcated lugs 341 each having a through hole 340. The upper joint knuckle 301 is also equipped with a rotation adjustment 303 having a round hole 344 which is engaged with a spinning shaft 356 disposed under the cast mounting platform 35 so that the cast mounting platform 35 can be rotatably adjusted.

The lower joint knuckle 302 has a joint tube 331 having a through hole 330. In assembly, the joint tube 331 is disposed between the two lugs with the through hole 330 in alignment with the through hole 340 and a sleeve 345 is led through the aligned holes, then a locking member 343 is engaged with each end of the sleeve 345. A turning knob 342 having threads thereon is engaged with the locking members 343 one of which is provided with inner threads so that the upper joint knuckle 301 can be rotatably actuated with respect to the lower joint knuckle 302.

The lower joint knuckle 302 is provided with a coupling section 33 having a through hole 332 having an axis oriented orthogonally with respect to the axis of the joint tube 331 which is fitted in between the bifurcated lugs 341. A. through hole 334 is disposed on the wall of the coupling section so as to permit a turning knob 333 to be engaged therewith.

The supporting block 32 is provided with a horizontal extension axis 323 which is engaged with the through hole 332 of the coupling section 33. A vertical point hole 322 is disposed at one end of the supporting block 32 so that the supporting block 32 can be rotatably mounted onto the operation base 31 by means of a vertical rod 311. The bottom end of the operation base 31 is engaged with a pair of bolts 40 that are removably disposed in the slots 12 so that the location of the operation base 31 can be adjusted. A turning knob 321 is in locking engagement with the supporting block 32 so that the supporting block 32 is firmly secured in place onto the operation base 31 when the turning knob 321 is screwed tight. To permit the supporting block 32 to be rotatably adjusted, the turning knob 321 must be loosened.

The threaded turning knobs 321, 333, 342 and 346 are used to firmly lock the joint knuckles and the supporting block 32 and the cast mounting platform 35 in place so that the upper joint upper joint knuckle 301, the lower joint knuckle 302 and the supporting block 32 and the cast mounting platform 35 can be adjusted with respect to one another and locked in place.

Figure 14:
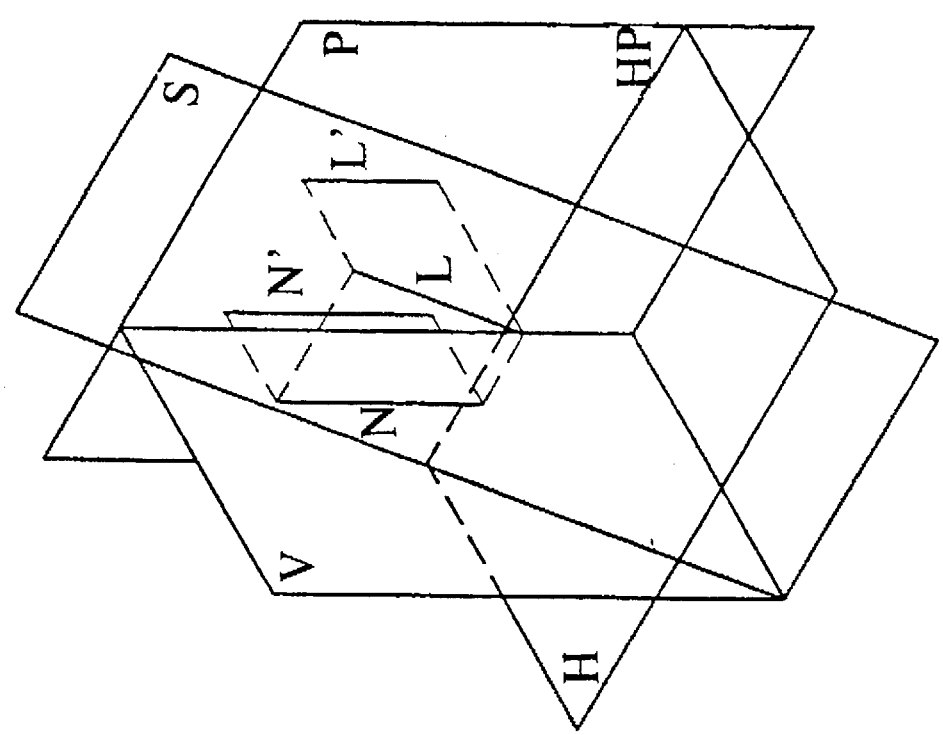
FIG. 14 is a diagram showing the reference planes V, P, H, of the project geometry; plane S represents the cast surface; line N representing the analyzing rod is perpendicular to the horizontal plane H; line L represents a scoring line on the plane S; if the line L is made in coincidence with the line N, then let the plane S rotate about the line HP which is the intersection of plane H and plane P; the line L is perpendicular to the line HP, so the projection of the line L on the plane P (line L') will always be parallel to the projection of line N on the plane P (line N'); whenever the plane S is rotated about the line HP or a parallel line, this relationship will not vary, i.e., the scoring lines parallel to the projection of the analyzing rod on the cast surface.

Referring to FIG. 14, to carry out the scoring method, detailed steps are given as follows:

If a line is scored in coincidence with the analyzing rod, and the cast is tilted in a direction perpendicular to the cast surface, the scored line will always be the projection of the analyzing rod on the cast surface. By tilting the cast in this manner until the line on the other side of the cast is again parallel to the analyzing rod, the original cast position is reproduced.

1. When the cast surface abuts closely against a reference plane created by the two parallel pillars 355 of the cast mounting platform 35 and the rotation adjustment is set at zero, it is perpendicular to the long axis of the upper joint knuckle. This relationship will not be varied in any lateral tilt setting.

2. The long axes of the upper joint knuckle and the lower joint knuckle are perpendicular to each other. So, the cast surface (in any lateral tilt setting) will be always parallel to the long axis of the lower joint knuckle.

3. The lower joint knuckle restricts the movement of the cast in a direction perpendicular to the base of the cast. So, when the line on the base of the cast has been adjusted parallel to the analyzing rod, this relationship will always be maintained, i.e., the projection of the analyzing rod on the base of the cast) at any anteroposterior tilt setting.

Figure 15B:
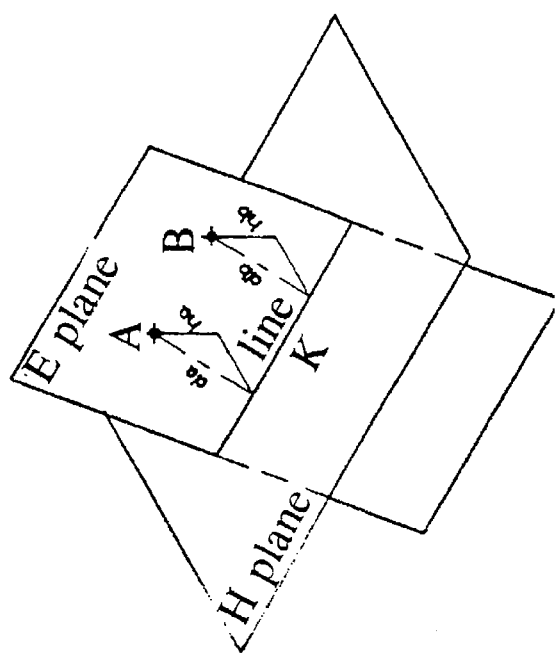
FIG. 15b shows the tilting of the plane E in a perpendicular direction by actuation of the upper joint knuckle so as to put points A and B on a different level; then the plane E is rotated to make the points A and B on an identical level again; at this position the height ha is equal to the height hb, so the distance of point A to the line K (the intersection line of planes E and H) da will become equal to the distance db from point B to the line K; whenever the plane E is rotated about the line K or a parallel line, points A and B will always be on an identical level.
Figure 15A:
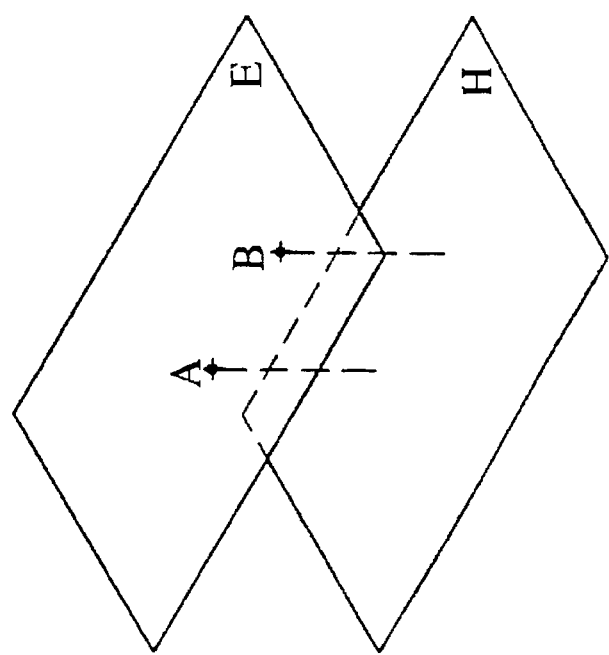
FIG 15a is a diagram showing two points A and B of the tripod mark method; if points A and B are adjusted to be on an identical level (using height adjustment screws along with the analyzing rod when the cast mounting platform is parallel with the horizontal plane) with the cast mounting platform, they will always be on the same plane (plane E) created by the movement of the cast mounting platform controlled by rotation adjustment.

For the tripod-marks method:

Referring to FIGS. 15A, 15B, if two points of the tripod-marks are to be put on an identical level, the cast is tilted in a direction perpendicular to the line created by the two points, the two points will alawys be located at the same level. By tilting the cast in this manner until all three points are put on the same level, the original east position is reproduced.

1. When the upper joint knuckle and the lower joint knuckle are set at zero degree, the cast mounting platform will be parallel to the horizontal plane. By means of the height adjustment screws, two points of the tripod-marks can be placed on the same level as the cast mounting platform. Under this circumstance, the two points will be located on the same plane created by rotation of the rotation adjustment.

2. Afterwards, the cast mounting platform is tilted in the perpendicular direction by means of the upper joint knuckle, the two points will be placed on a different level.

3. The cast mounting platform can be rotated by way of the rotation adjustment until the two points are disposed on an identical level again. At this position, the line connecting these two points will just become perpendicular to the direction of movement of the upper joint knuckle. So, this time the two points will always be placed on an identical level to each other at any tilt setting controlled by the upper joint knuckle.

Figure 16:
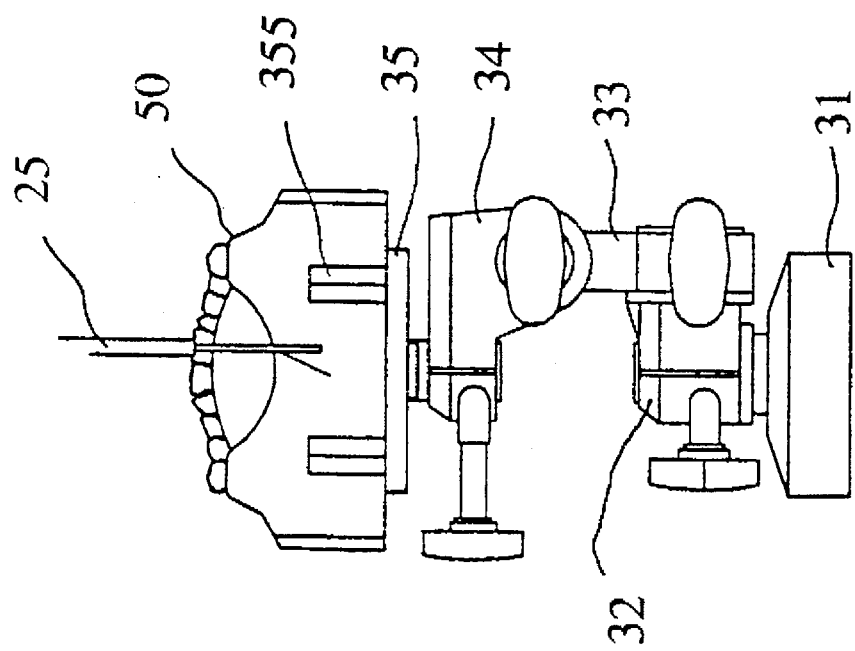
FIG. 16 is a diagram showing the mounting of a cast onto the cast mounting platform with the cast surface in close abutment with the two parallel pillars and then locking the cast at this position and setting the rotation adjustment at zero degree.

Detailed procedures for manipulation of this surveyor table are given as below:

For the scoring method:

1. First put the cast on the cast mounting platform, the base of the cast faces the reference plane created by the two parallel pillars; it is necessary to keep the base of the cast in close abutment against the reference plane and then lock it at this position. To secure the cast position, if there is a space under the cast, due to the border of the cast not being squarely angled, it can be supported in place by the height adjustment screws, as shown in FIG. 16.

2. Set the rotation adjustment at zero degree, then the reference plane will be perpendicular to the long axis of the upper joint knuckle.

Figure 17:
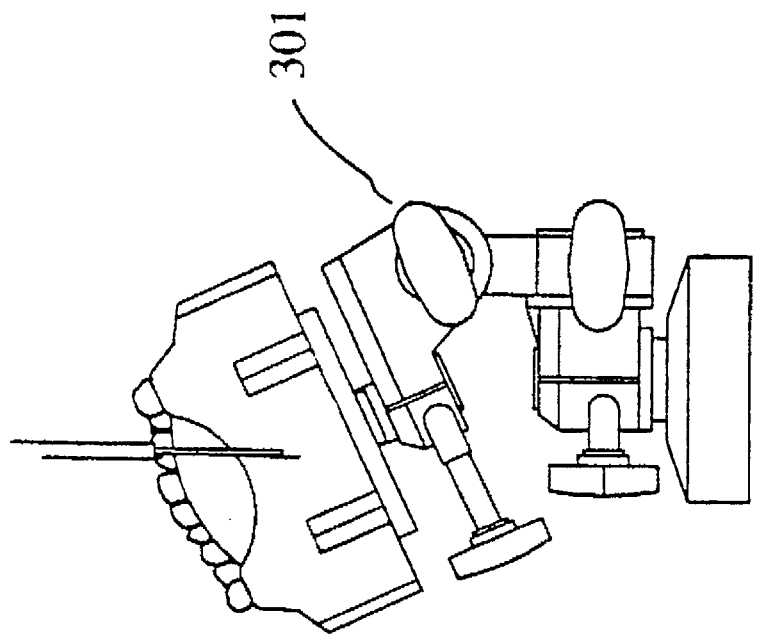
FIG. 17 shows the tilting of the cast by way of the upper joint knuckle so as to make the scoring line parallel to the analyzing rod and then lock the upper joint knuckle at this position.

3. Use the upper joint knuckle to make adjustment on the lateral tilting of the cast to make the line on the base of the cast parallel to the analyzing rod. Then lock the upper joint knuckle at this setting, as shown in FIG. 17.

Figure 18B:
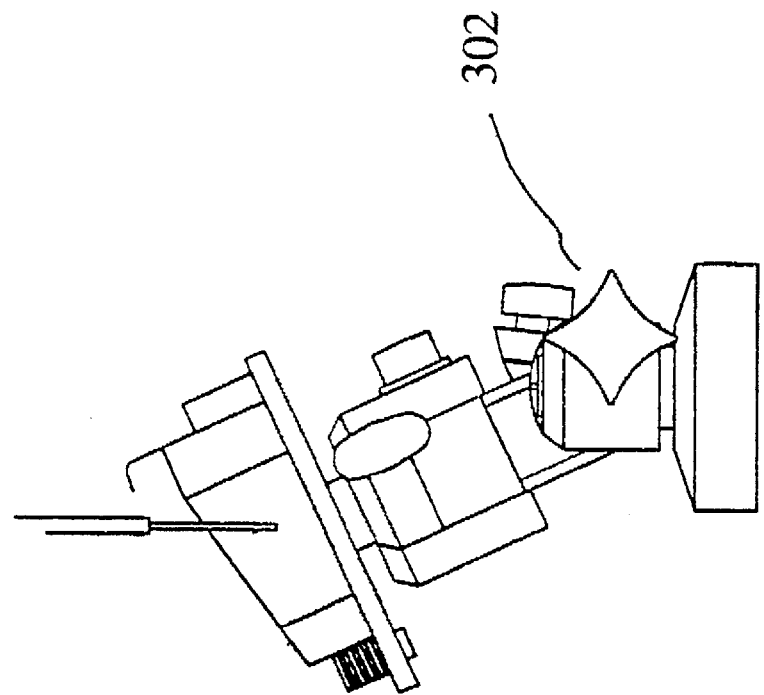
FIGS. 18a, 18b show the use of the lower joint knuckle to tilt the cast to make the scoring line on the lateral surface of the cast parallel to the analyzing rod then lock the lower joint knuckle at this position whereby the cast position is reestablished.
Figure 18A:
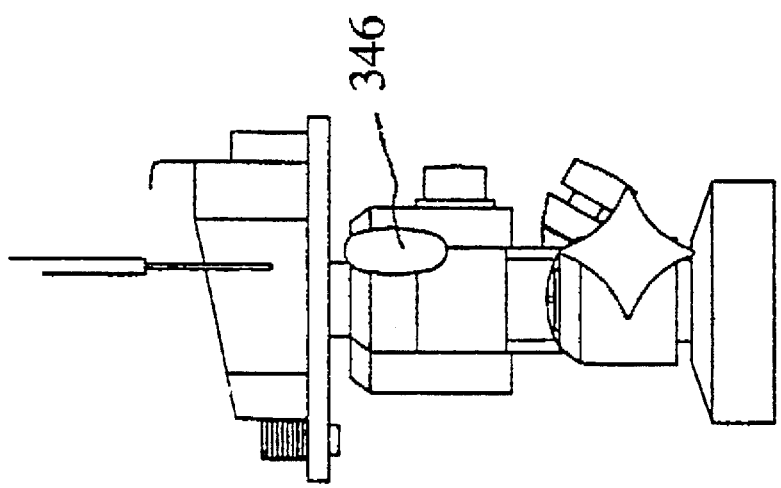

4. Use the lower joint knuckle to adjust the anteroposterior tilting of the cast to make the line on lateral side of the cast parallel to the analyzing rod. Then lock the lower joint knuckle at this setting, as shown in FIGS. 18a, 18b.

For the tripod-masks method:

1. Set the upper joint knuckle and lower joint knuckle at zero degree, as shown in FIG. 19.

Figure 20:
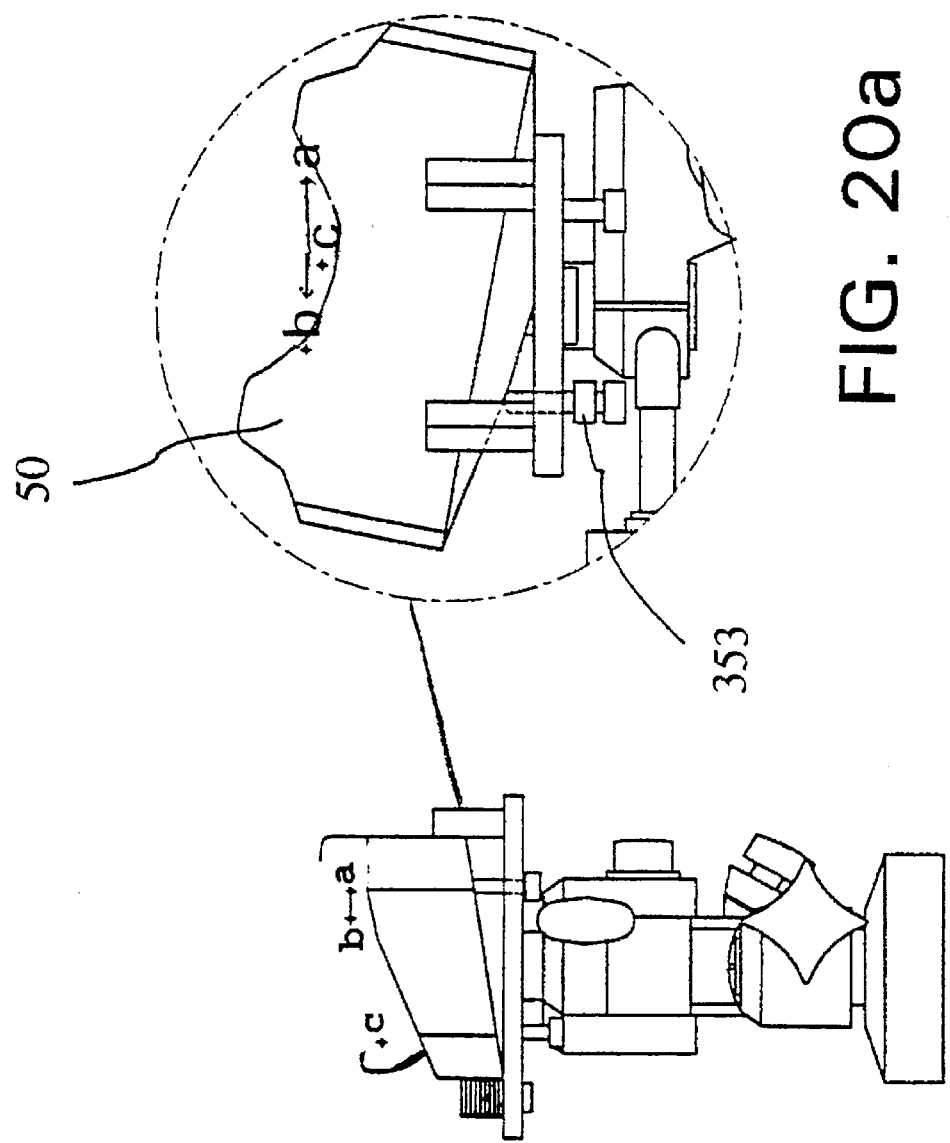

2. Make the two points of the tripod-marks on the same level by actuation of the height adjustment screws, then lock the cast at this position, as shown in FIG. 20.

Figure 21:
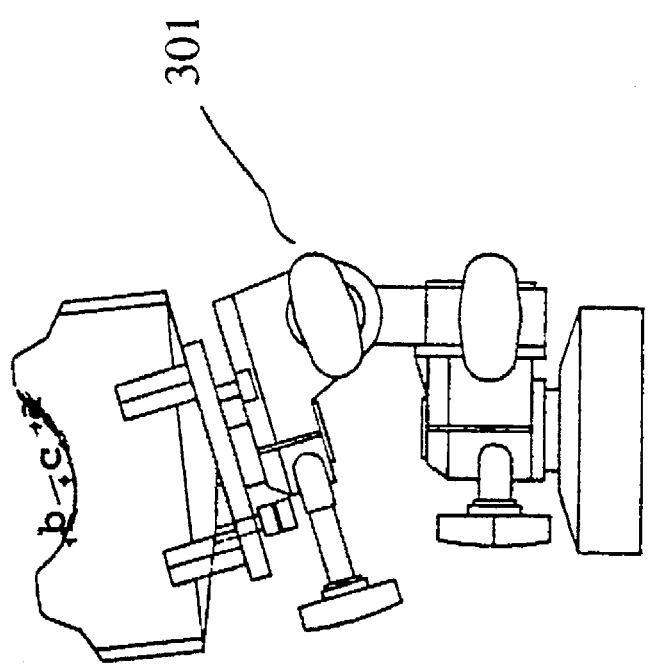
FIG. 21 shows the use of the upper joint knuckle to tilt the cast mounting platform in a perpendicular direction, points a and b being put on a different level.

3. Use the upper joint knuckle to tilt the cast mounting platform in a perpendicular direction. The lower joint knuckle is locked at zero degree setting, as shown in FIG. 21.

Figure 22:
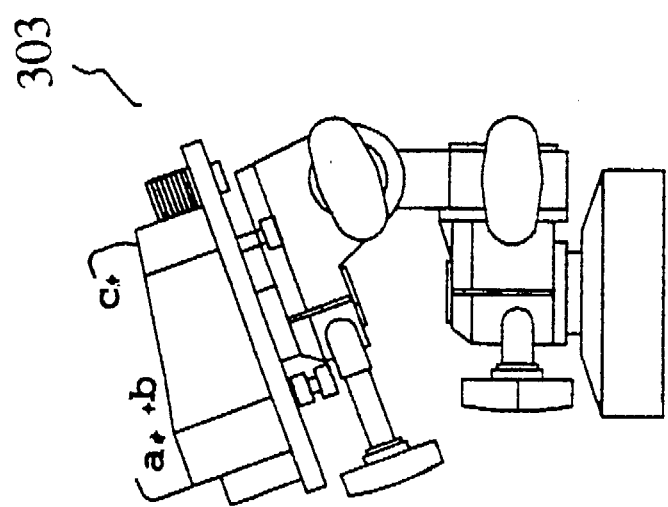
FIG. 22 shows the rotation of the cast mounting platform about the rotation adjustment so as to make the points a and b on an identical level again and then locking the rotation adjustment at this position.

4. Rotate the cast mounting platform by way of the rotation adjustment until the two points are located on the same level again, then lock the rotation adjustment at this setting, as shown in FIG. 22.

Figure 23B:
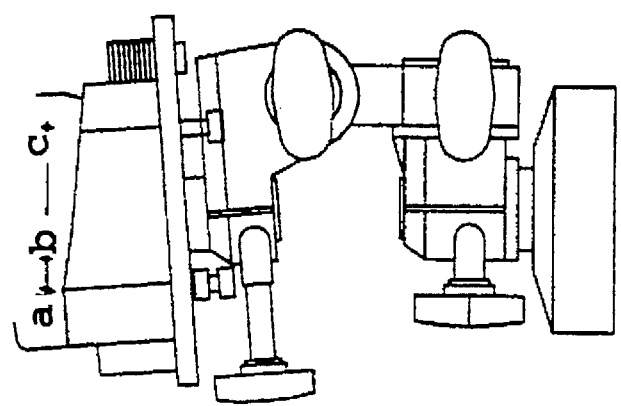
FIGS. 23a, 23b show the tilting of the cast mounting platform about the upper joint knuckle to make the point c on an identical level with the points a and b then locking the upper joint knuckle at this position, the cast position being reestablished.
Figure 23A:
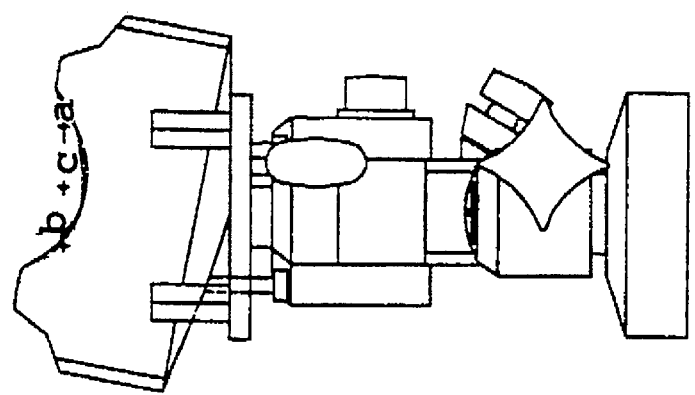

5. Tilt the cast mounting platform around the upper point knuckle, all three points can then be made on the same level, as shown in FIGS. 23A, 23B.

The selection of the path of insertion is described as follows:

It has been suggested that cast be thought of as having only two axes, permitting only anteroposterior and lateral tilting. The sequences of determination are cited in ref. 4:

1. guiding planes
2. retentive areas
3. interference
4. esthetics

So, the anteroposterior tilting of the cast orientation should be dertermined first, then is the lateral tilting. Detailed steps thereof are listed as follows:

1. Select two corresponding points, for example, the cusp tip of bilateral first premolars, on the cast.
2. Set the upper and lower joint knuckles at zero degree. Put these two points on an identical level by means of height adjusting screws, then lock the cast at this position.
3. Tilt the cast mounting platform by the upper joint knuckle, causing these points to be on different levels.
4. Get the cast mounting platform rotated by way of the rotation adjustment until these points are put on an identical level again, then lock the rotation adjustment at this position. This time the direction of cast movement can be determined by simple anteroposterior or lateral tilting seperately.
5. Use the upper joint knuckle to set the antereoposterior tilting of the cast according to the guiding planes.
6. Use the lower joint knuckle to set the lateral tilting of the cast according to the retentive areas selected.
7. Afterwards, modify the cast orientation to circumvent the problems of interferences and esthetics.

In summary, to precisely record and reproduce the path of insertion of a cast on surveyors is very important. By means of simple geometric concepts in this study, method to improve the accuracy of scoring line makings, the present invention provides a special scoring tool and a new surveyor table. This system has many advantages in practical applications, it not only can quickly and accurately reorient the cast position on surveyors, but the surveyor table also has advantages in selection of the path of insertion of a cast because the tilt of the cast in lateral tilting and antereoposterior tilting can be separately analyzed. The convenience and accuracy in manipulation makes the surveyor table of the present invention widely accepted in this field in the future.

I claim:

1. An apparatus for recording and reproducing the path of insertion of a cast on dental surveyor, comprising:
   a surveyor having a horizontally disposed supporting base and a vertically disposed post which is mounted to said supporting base;
   a first arm having one end pivotally fixed to said vertical post;
   a second arm having one end pivotally connected to the other end of said first arm;
   an adjustable rod vertically disposed at the other end of said second arm;
   a scoring tool for scoring marks on a cast being attached to the bottom end of said adjustable rod;
   an operation base being rotatably mounted to supporting base;
   a supporting block engaged with said operation base, rotatable in a horizontal plane;
   a lower joint knuckle engaged with said supporting block being rotatable in a vertical plane with respect to said supporting block;
   an upper joint knuckle engaged with said lower joint knuckle being rotatable with respect thereto in a vertical plane;
   a cast mounting platform engaged with said upper joint knuckle being rotatable with respect thereto in a horizontal plane;
   said mounting platform having adjusting means associated therewith so as to permit a dental cast to be adjustably mounted thereto.

2. An apparatus for recording and reproducing the path of insertion of a cast on dental surveyor, as claimed in claim 1 wherein
   the operation base has a vertical axis at the center thereof being adjustably fixed to said supporting base;
   the supporting block is rotatably engaged with said vertical axis of said operation base, permitting said supporting block to rotate in a horizontal plane, having a horizontal extension axis;
   said lower joint knuckle has a joint tube and a coupling section where said coupling section is rotatably engaged with said horizontal extension axis of said supporting block permitting said lower joint knuckle to be rotatably adjusted in a vertical plane;
   said joint tube is integrally engaged with said coupling section in such a manner that its axial direction is orthogonal to the axial direction of said joint tube;
   the upper joint knuckle includes bifurcated lugs with said joint tube rotatably fitted therebetween so as to permit said upper joint knuckle to be rotatably adjusted in a vertical plane and an extended rotation adjustment portion;
   the adjustable cast mounting platform has a pair of parallel fixed pillars in cooperation with a spring biased clamp for limiting a cast mounted thereon in place; and
   said adjustable cast mounting platform is rotatably engaged with said extended rotation adjustment portion of said upper joint knuckle so as to be rotatable in a horizontal plane for adjustment;
   whereby a cast secured to said cast mounting platform can be randomly adjustably tilted in three dimensions in cooperation with said pivotal first arm and second arm and said vertically adjustable rod so as to permit said adjustable rod to be placed in abutment against said cast accurately for recording and reproducing the path of insertion of a cast easily.

3. An apparatus as claimed in claim 2 wherein said upper joint knuckle and said joint tube of said lower joint knuckle are provided with a combination zero-setting mark so as to permit said upper joint knuckle to be reset with ease in a right-angle relation with respect to said lower joint knuckle.

4. An apparatus for recording and reproducing the path of insertion of a cast on dental surveyor as claimed in claim 2 wherein said scoring tool has a mandrel and an analyzing rod pivotally connected to each other by a hinge joint and said analyzing rod has a rectangular cross section.

5. An apparatus for recording and reproducing the path of insertion of a cast on dental surveyor as claimed in claim 2 wherein said supporting block rotatably mounted to said operation base is lockable in place by a locking means so as to prevent the supporting block from rotation after setting.

6. An apparatus for recording and reproducing the path of insertion of a cast on dental surveyor as claimed in claim 2 wherein said lower joint knuckle is rotatably engaged with said supporting block by way of said coupling which section is provided with a locking means to lock said lower joint knuckle in place for preventing said lower joint knuckle from rotation after setting.

7. An apparatus as claimed in claim 2 wherein said upper joint knuckle rotatably engaged with said lower joint knuckle is provided with a first locking means for locking said upper and lower joint knuckles in place so as to prevent the same from rotating with respect to each other.

8. An apparatus as claimed in claim 2 wherein said upper joint knuckle is provided with a second locking means for locking said rotatable cast mounting platform mounted to said upper joint knuckle in place.

9. An apparatus as claimed in claim 2 further comprising a spring bias urging clamp wherein said cast mounting platform has an open ended slot in which said spring biased urging clamp is slidably adjusted and said cast mounting platform is provided with at least 3 height adjustment screws for abutting the bottom of a located cast to vary the level thereof.

10. An apparatus as claimed in claim 2 wherein said rotation adjustment portion of said upper joint knuckle is provided with a combination zero-setting mark for facilitation of putting said cast mounting platform in a right-angle relation with respect to said upper joint knuckle.

11. An apparatus for recording and reproducing the path of insertion of a cast on dental surveyor as claimed in claim 1 wherein said scoring tool has a mandrel and an analyzing rod pivotally connected to each other by a hinge joint and said analyzing rod has a rectangular cross section.

12. An apparatus for recording and reproducing the path of insertion of a cast on dental surveyor as claimed in claim 1 wherein said supporting block rotatably mounted to said operation base is lockable in place by a locking means so as to prevent the supporting block from rotation after setting.

13. An apparatus for recording and reproducing the path of insertion of a cast on a dental surveyor as claimed in claim 1 wherein said lower joint knuckle is rotatably engaged with said supporting block by way of a coupling section where said coupling section is provided with a locking means to lock said lower joint knuckle in place for preventing said lower joint knuckle from rotation after setting.

14. An apparatus as claimed in claim 13 wherein said coupling section of said lower joint knuckle and said supporting block are provided with a combination zero-setting mark so as to permit said lower joint knuckle to be reset with ease in a right-angle relation with respect to said supporting block.

15. An apparatus as claimed in claim 1 wherein said upper joint knuckle rotatably engaged with said lower joint knuckle is provided with a first locking means for locking said upper and lower joint knuckles in place so as to prevent the same from rotating with respect to each other.

16. An apparatus as claimed in claim 1 wherein said upper joint knuckle is provided with a second locking means for locking said rotatable cast mounting platform mounted to said upper joint knuckle in place.

17. An apparatus as claimed in claim 1 further comprising a spring bias urging clamp and wherein said cast mounting platform has an open ended slot in which said spring biased urging clamp is slidably adjusted and said cast mounting platform is provided with at least 3 height adjustment screws for abutting the bottom of a located cast to vary the level thereof.

18. An apparatus as claimed in claim 1 wherein said upper joint includes a rotation adjustment portion knuckle is provided with a combination zero-setting mark for facilitation of putting said cast mounting platform in a right-angle relation with respect to said upper joint knuckle.

19. A method of recording and reproducing the path of insertion onto a cast mounting platform including two parallel pillars of a dental cast with a base having lines formed thereon on a dental surveyor which is marked with a plurality of marks including a zero setting mark and includes an elongated upper joint knuckle defining a long axis, a lower joint knuckle, and an analyzing rod, the method comprising the steps of:

locating the dental cast having a number of separated marks on the sides of the base of the cast on the cast mounting platform with the cast facing a reference plane which is created by said two parallel pillars, keeping the base of said cast in close contact with said reference plane, then locking said cast at this position;

setting by rotation adjustment to zero degree by means of said zero-setting mark, making said reference plane perpendicular to the long axis of said upper joint knuckle;

using said upper joint knuckle to adjust the lateral tilting of said cast to make a line on the base of said cast parallel to said analyzing rod, then locking said upper joint knuckle at this setting; and using said lower joint knuckle to adjust the anteroposterior tilting of said cast to make a line on a lateral side of said cast parallel to said analyzing rod, then locking said lower joint knuckle at this setting.

20. The method of claim 19 where the base includes a plurality of height adjustment set screws and a tripod mark and further comprises the steps of:

setting said upper joint and lower joint knuckles at zero degree by means of said zero-setting marks;

making two points of said tripod-mark at equal level by adjusting said height adjustment screws, then locking said cast at this position;

using said upper joint knuckle to tilt said cast mounting platform in a perpendicular direction with said lower joint knuckle locked at zero degree setting;

using said rotation adjustment to rotate said cast mounting platform until the two points reach equal level again, then locking said rotation adjustment at this setting; and tilting said cast mounting platform around said upper joint knuckle to make all three points at the same level.

\* \* \* \* \*